United States Patent [19]

Mencke et al.

[11] Patent Number: 5,712,295
[45] Date of Patent: Jan. 27, 1998

[54] AGONISTS AND ANTAGONISTS OF THE NICOTINIC ACETYLCHOLINE RECEPTORS OF INSECTS TO CONTROL ENDOPARASITES

[75] Inventors: Norbert Mencke, Leverkusen; Achim Harder, Köln, both of Germany; Terence Hopkins, Tambourene, Australia

[73] Assignee: Bayer Aktiengesellschaft, Leverkusen, Germany

[21] Appl. No.: 750,012

[22] PCT Filed: May 26, 1995

[86] PCT No.: PCT/EP95/02014

§ 371 Date: Nov. 21, 1996

§ 102(e) Date: Nov. 21, 1996

[87] PCT Pub. No.: WO95/33453

PCT Pub. Date: Dec. 14, 1995

[30] Foreign Application Priority Data

Jun. 7, 1994 [DE] Germany ............... 44 19 814.0

[51] Int. Cl.$^6$ ............... A61K 31/44; A61K 31/675; A61K 31/54; A61K 31/425
[52] U.S. Cl. ............... 514/338; 514/91; 514/226.8; 514/338; 514/339; 514/357; 514/365; 514/385
[58] Field of Search ............... 514/341, 91, 226.8, 514/338, 339, 357, 365, 385

[56] References Cited

U.S. PATENT DOCUMENTS

| | | | |
|---|---|---|---|
| 4,678,795 | 7/1987 | Shiokawa et al. | 514/341 |
| 4,812,571 | 3/1989 | Shiokawa et al. | 546/296 |
| 4,988,712 | 1/1991 | Shiokawa et al. | 514/340 |
| 5,298,507 | 3/1994 | Shiokawa et al. | 514/256 |
| 5,504,081 | 4/1996 | Lohr et al. | 514/225 |

FOREIGN PATENT DOCUMENTS

| | | |
|---|---|---|
| 689474 | 6/1964 | Canada. |
| 0 398 084 A3 | 11/1990 | European Pat. Off.. |

OTHER PUBLICATIONS

Pinnock, et al., Neuropharmacology, vol. 27, No. 8, pp. 843–848, Aug. 1988.
The Merck Index, 11th ed. p. 1030, cit# 6434, 1989.

*Primary Examiner*—Raymond Henley, Jr.
*Attorney, Agent, or Firm*—Sprung Kramer, Schaefer & Briscoe

[57] ABSTRACT

Use of agonists and antagonists of the nicotinergic acetylcholine receptors of insects for combating endoparasites is disclosed.

20 Claims, No Drawings

AGONISTS AND ANTAGONISTS OF THE NICOTINIC ACETYLCHOLINE RECEPTORS OF INSECTS TO CONTROL ENDOPARASITES

This is a 371 PCT /EP95/02014 filed May 26, 1995.

The present invention relates to combating endoparasites by means of agonists or antagonism of the nicotinergic acetylcholine receptors of insects.

Agonists or antagonists of the nicotinergic acetylcholine receptors of insects are known. They include the nicotinile insecticides and, very particularly, the chloronicotinile insecticides. It is also known that these compounds have an outstanding action against plant-injurious insects. The systemic action of these compounds in plants against plants-injurious insects is also known.

PCT Application WO 93/24 002 discloses that certain 1-[N-(halo-3-pyridylmethyl)]-N-methylamino-1-alkylamino-2-nitroethylene derivatives are suitable for systemic use against fleas in domestic animals. In this type of application, the active compound is administered to the domestic animal by oral or parenteral route, for example by means of an injection, to reach the blood stream of the domestic animal. The fleas then take up the active compound when they suck blood. However, nothing has been disclosed about an action of these compounds against endoparasites.

Surprisingly, it has now been found that agonists or antagonists of the nicotinergic acetylcholine receptors of insects are suitable for combating endoparasites.

Agonists or antagonists of the nicotinogenic acetylcholine receptors of insects are disclosed, for example, in European Published Application Nos. 464 830, 428 941, 425 978, 386 565, 383 091, 375 907, 364 844, 315 826, 259 738, 254 859, 235 725, 212 600, 192 060, 163 855, 154 178, 136 636, 303 570, 302 833, 306 696, 189 972, 455 000, 135 956, 471 372, 302 389; German Offenlegungsschrift Nos. 3 639 877, 3 712 307; Japanese Published Application Nos. 03 220 176, 02 207 083, 63 307 857, 63 287 764, 03 246 283, 04 9371, 03 279 359, 03 255 072; U.S. Pat. Nos. 5,034,524, 4,948,798, 4,918,086, 5,039,686, 5,034,404; PCT Application Nos. WO 91/17 659, 91/4965; French Application No. 2 611 114; Brazilian Application No. 88 03 621.

Reference is thus made expressly to the methods, processes, formulae and definitions described in these publications and to the individual preparations and compounds described therein.

These compounds can preferably be represented by the general formula (I)

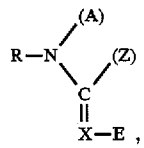

in which

R represents hydrogen, optionally substituted radicals from the group consisting of acyl, alkyl, aryl, aralkyl, heteroaryl or heteroarylalkyl.

A represents a monofunctional group from the series consisting of hydrogen, acyl, alkyl and aryl or represents a bifunctional group linked to the radical Z;

E represents an electron-attracting radical;

X represents the radicals —CH= or =N—, it being possible for the radical —CH= to be linked to the radical Z instead of an H atom;

Z represents a monofunctional group from the series consisting of alkyl, —O—R, —S—R,

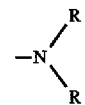

or represents a bifunctional group linked to the radical A or the radical X.

Particularly preferred compounds of the formula (I) are those in which the radicals have the following meanings:

R represents hydrogen and optionally substituted radicals from the series consisting of acyl, alkyl, aryl, aralkyl, heteroaryl, heteroarylalkyl.

Acyl radicals which may be mentioned are formyl, alkylcarbonyl, arylcarbonyl, alkylsulphonyl, arylsulphonyl, (alkyl-)-(aryl-)-phosphoryl, all of which can, in turn, be substituted.

Alkyl radicals which may be mentioned are $C_{1-10}$-alkyl, in particular $C_{1-4}$-alkyl, specifically methyl, ethyl, i-propyl and sec- or t-butyl, all of which can, in turn, be substituted.

Aryl radicals which may be mentioned are phenyl and naphthyl, in particular phenyl.

Aralkyl radicals which may be mentioned are phenylmethyl and phenethyl.

Heteroaryl radicals which may be mentioned are heteroaryl having up to 10 ring atoms and N, O and S, in particular N, as hetero atoms. Thienyl, furyl, thiazolyl, imidazolyl, pyridyl, benzthiazolyl may be mentioned specifically.

Heteroarylalkyl radicals which may be mentioned are heteroarylmethyl and heteroarylethyl having up to 6 ring atoms and N, O and S, in particular N, as hetero atoms.

Substituents which may be mentioned by way of example and as being preferred are:

alkyl having preferably 1 to 4, in particular 1 or 2, carbon atoms such as methyl, ethyl, n- and i-propyl and n-, i- and t-butyl; alkoxy having preferably 1 to 4, in particular 1 or 2, carbon atoms such as methoxy, ethoxy, n- and i-propyloxy and n-, i- and t-butyloxy; alkylthio having preferably 1 to 4, in particular 1 or 2, carbon atoms such as methylthio, ethylthio, n- and i-propylthio and n-, i- and t-butylthio; halogenoalkyl having preferably 1 to in particular I to 2 carbon atoms and preferably 1 to 5, in particular 1 to 3, halogen atoms, the halogen atoms being identical or different and being represented preferably by fluorine, chlorine or bromine, in particular fluorine, such as trifluoromethyl; hydroxyl, halogen, preferably fluorine, chlorine, bromine and iodine, in particular fluorine, chlorine and bromine; cyano, nitro; amino; monoalkyl- and dialkylamino having preferably 1 to 4, in particular 1 or 2, carbon atoms per alkyl group, such as methylamino, methyl-ethyl-amino, n- and i-propylamino and methyl-n-butylamino; carboxyl, carbalkoxy having preferably 2 to 4, in particular 2 or 3, carbon atoms, such as carbomethoxy and carboethoxy; sulpho (—$SO_3H$); alkylsulphonyl having preferably 1 to 4, in particular 1 or 2, carbon atoms, such as methylsulphonyl and ethylsulphonyl; arylsulphonyl having preferably 6 or 10 aryl carbon atoms, such as phenylsulphonyl, and also heteroarylamino and heteroarylalkylamino, such as chloropyridylamino and chloropyridylmethylamino.

A particularly preferably represents hydrogen and optionally substituted radicals from the series consisting of acyl, alkyl and aryl which preferably have the meanings given under R. A furthermore represents a bifunctional group. A group which may be mentioned is optionally substituted alkylene having 1–4, in particular 1–2, C atoms, substituents which may be mentioned being those substituents listed further above, and it being possible for the alkylene groups to be interrupted by heteroatoms from the series consisting of N, O and S.

A and Z together with the atoms to which they are bonded can form a saturated or unsaturated heterocyclic ring. The heterocyclic ring can contain another 1 or 2 identical or different hetero atoms and/or hetero groups. Hetero atoms are preferably represented by oxygen, sulphur or nitrogen and hetero groups by N-alkyl, the alkyl of the N-alkyl group preferably containing 1 to 4, in particular 1 or 2, carbon atoms. Alkyl radicals which may be mentioned are methyl, ethyl, n- and i-propyl and n-, i- and t-butyl. The heterocyclic ring contains 5 to 7, preferably 5 or 6, ring members.

Examples of the heterocyclic ring which may be mentioned are pyrrolidine, piperidine, piperazine, hexamethyleneimnine, Hexahydro-1,3,5-triazine, morpholine, all of which can optionally be substituted, preferably by methyl.

E represents an electron-withdrawing radical, radicals which may be mentioned being, in particular, $NO_2$, CN, halogenoalkylcarbonyl, such as 1,5-halogeno-$C_{1-4}$-carbonyl, in particular $COCF_3$.

X represents —CH= or —N=

Z represents optionally substituted radicals alkyl, —OR, —SR, —NRR or, R and the substituents preferably having the abovementioned meaning.

Z, in addition to the abovementioned ring, together with the atom to which it is bonded and the radical

instead of X can form a saturated or unsaturated heterocyclic ring. The hterocyclic ring can contain a further 1 or 2 identical or different hetero atoms and/or hetero groups. Hetero atoms are preferably represented by oxygen, sulphur or nitrogen and hetero groups by N-alkyl, the alkyl or N-alkyl group preferably containing 1 to 4, in particular 1 or 2, carbon atoms. Alkyl radicals which may be mentioned are methyl, ethyl, n- and i-propyl and n-, i- and t-butyl. The heterocyclic ring contains 5 to 7, preferably 5 or 6, ring members.

Examples of the heterocyclic ring which may be mentioned are pyrrolidine, piperidine, piperazine, hexamethyleneimine, morpholine and N-methylpiperazine.

Compounds which can be used very particularly preferably according to the invention are the compounds of the general formulae (II) and (III):

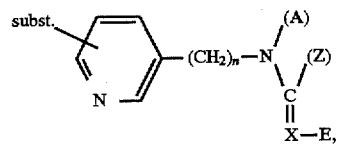

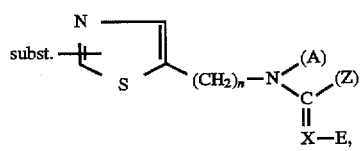

in which n represents 1 or 2,

Subst. represents one of the abovementioned substituents, in particular halogen, very particularly chlorine, A, Z, X and E have the abovementioned meanings.

The following compounds may be mentioned specifically:

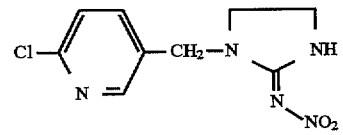

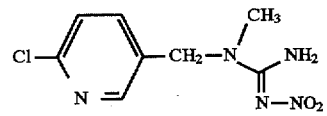

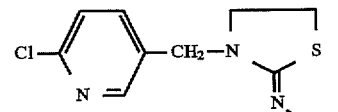

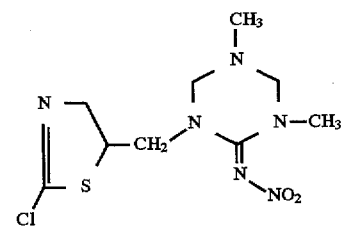

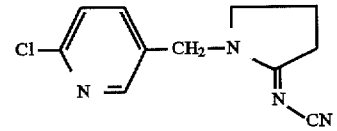

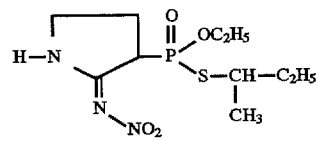

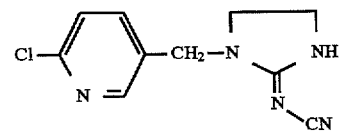

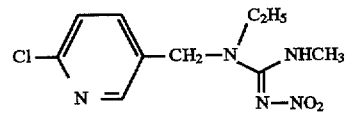

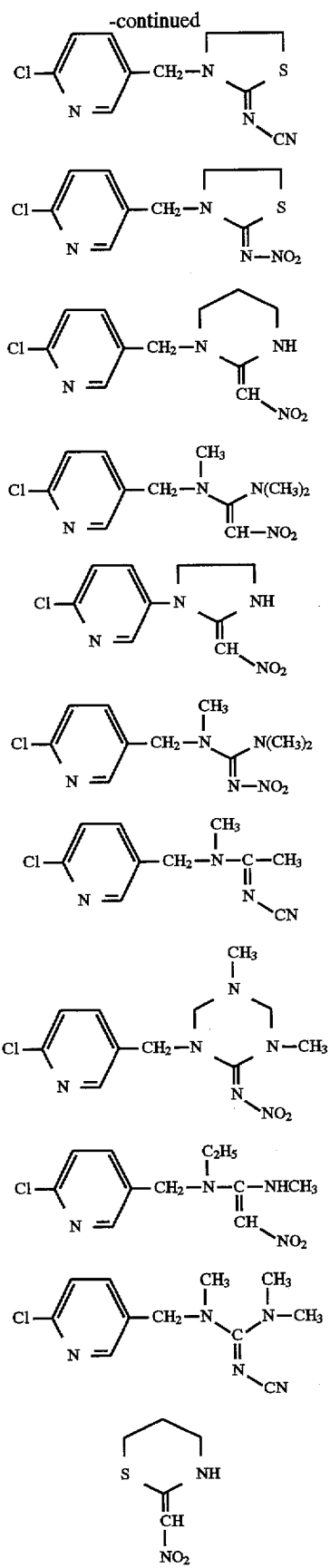

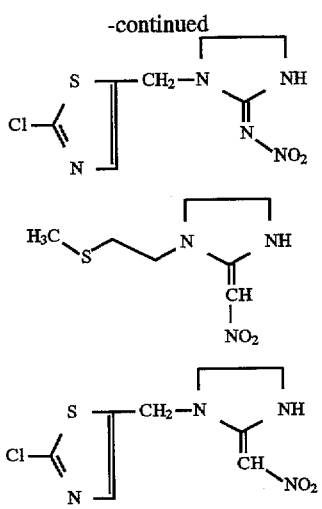

While having a favourable toxicity to warm-blooded species, the active compounds are suitable for combating pathogenic endoparasites which are found in humans and in animal keeping and livestock breeding, in productive livestock, breeding animals, zoo animals, laboratory animals, experimental animals and pets. In this context, they are active against all or individual stages of development of the pests and against resistant and normally-sensitive species. By combating the pathogenic endoparasites, it is intended to reduce disease, deaths and decreasing performance (for example in the production of meat, milk, wool, hides, eggs, honey etc.) and, where appropriate, transmission to humans, so that more economic and simpler animal keeping is possible by using the active compounds. The pathogenic endoparasites include Cestodes, Trematodes and Nematodes, in particular:

From the order of the Pseudophyllidea, for example: *Diphyllobothrium spp., Spirometra spp., Schistocephalus spp., Ligula spp., Bothridium spp., Diphlogonoorus spp..*

From the order of the Cyclophyllidea, for example: *Mesocestoides spp., Anoplocephala spp., Paranoplocephala spp., Moniezia spp., Thysanosmsa spp., Thysaniezia spp., Avitellina spp., Stilesia spp., Cittotaenia spp., Anhyra spp., Bertiella spp., Taenia spp., Echinococcus spp., Hydratigera spp., Davainea spp., Raillietina spp., Hymenolepsis spp., Echinolepsis spp., Echinocotyle spp., Diorchis spp., Dipylidium spp., Joyeuxiella spp., Diplopylidium spp..*

From the subclass of the Monogenea, for example: *Cyrodactylus spp., Dactylogyrus spp., Polystoma spp..*

From the subclass of the Digenea, for example: *Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhloccelum spp., Paramphistomum spp., Calicophoron spp., Cotylophoron spp., Gigantocotyle spp., Fischoederius spp., Gastrothylacus spp., Notocotylus spp., Catatropis spp., Plagiorchis spp., Prosthogonismus spp., Dicrocoelium spp., Collyriclum spp., Nanophyetus spp., Opisthorchis spp., Clonorchis spp., Metorchis spp., Heterophyes spp., Metagonimus spp..*

From the order of the Enoplida, for example: *Trichuris spp., Capillaria spp., Trichlomosoides spp., Trichinella spp..*

From the order of the Rhabditia, for example: *Micronema spp., Strongyloides spp..*

From the order of the Strongylida, for example: *Stronylus spp., Triodontophorus spp., Oesophagodontus spp., Tricho-*

*nema spp., Gyalocephalus spp., Cylindropharynx spp., Poteriostromum spp., Cyclococercus spp., Cylicostephanus spp., Oesophagostomum spp., Chabertia spp., Stephanurus spp., Acylostoma spp., Uncinaria spp., Bunostomum spp., Globocephalus spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp..*

From the order of the Oxyurida, for example: *Oxyuris spp., Enterobius spp., Passalurus spp., Syphacia spp., Aspiculuris spp., Heterakis spp..*

From the order of the Ascaridia, for example: *Ascaris spp., Toxascaris spp., Toxocara spp., Parascaris spp., Anisakis spp., Ascaridia spp..*

From the order of the Spirurida, for example: *Gnathostoma spp., Physaloptera spp., Thelazia spp., Gongylonema spp., Habronema spp., Parabronema spp., Draschia spp., Dracunculus spp..*

From the order of the Filariida, for example: *Stephanofilaria spp., Parafilaria spp., Setaria spp., Loa spp., Dirofilaria spp., Litomosoides spp., Brugia spp., Wuchereria spp., Onchocerca spp..*

From the order of the Gigantohynchida, for example *Filicollis spp., Moniliformis spp., Macracanthorhynchus spp., Prosthenorchis spp..*

The productive livestock and breeding animals include mammals such as, for example, cattle, horses, sheep, pigs, goats, camels, water buffalo, donkeys, rabbits, fallow deer, reindeer, fur-bearing animals such as, for example, mink, chinchilla, racoon, birds such as, for example, chickens, geese, turkeys and ducks.

Laboratory animals and experimental animals include mice, rats, guinea pigs, golden hamsters, dogs and cats.

Pets include dogs and cats.

Administration can be effected prophylactically as well as therapeutically.

The active compounds are administered, directly or in the form of suitable preparations, enterally, parenterally, dermally, nasally, by environment treatment, or with the aid of active-compound-containing shaped articles such as, for example, strips, plates, bands, collars, ear marks, limb bands, marking devices.

The active compounds are administered enterally, for example orally, in the form of powders, suppositories, tablets, capsules, pastes, drinks, granules, drenches, boli, medicated feed or drinking water. Dermal administration is effected, for example, in the form of dipping, spraying bathing, washing, pouring-on and spotting-on, and dusting. Parenteral administration is effected, for example, in the form of an injection (intramuscular, subcutaneously, intravenous, intraperitoneal) or by implants.

Suitable preparations are:

Solutions such as injectable solutions or, oral solutions, concentrates for oral administration after dilution, solutions for use on the skin or in body cavities, pour-on and spot-on formulations, gels;

Emulsions and suspensions for oral or dermal administration and for injection; semi-solid preparations;

Formulations in which the active compound is incorporated in a cream base or in an oil-in-water or water-in-oil emulsion base;

Solid preparations such as powders, premixes or concentrates, granules, pellets, tablets, boli, capsules; aerosols and inhalants, shaped articles containing active compound.

Injectable solutions are administered intravenously, intramuscularly and subcutaneously.

Injectable solutions are prepared by dissolving the active compound in a suitable solvent and, if appropriate, adding additives such as solubilizers, acids, bases, buffer salts, antioxidants and preservatives. The solutions are sterile-filtered and drawn off.

The following may be mentioned as solvents: physiologically acceptable solvents such as water, alcohols such as ethanol, butanol, benzyl alcohol, glycerol, hydrocarbons, propylene glycol, polyethylene glycols, N-methyl-pyrrolidone, and mixtures of these.

If appropriate, the active compounds can also be dissolved in physiologically acceptable vegetable or synthetic oils which are suitable for injection.

The following may be mentioned as solubilizers: solvents which enhance solution of the active compound in the main solvent, or which prevent its precipitation. Examples are polyvinylpyrrolidone, polyoxyethylated castor oil, polyoxyethylated sorbitan esters.

Preservatives are: benzyl alcohol, trichlorobutanol, p-hydroxybenzoic esters, n-butanol.

Oral solutions are administered directly. Concentrates are administered orally after previously having been diluted to the administration concentration. Oral solutions and concentrates are prepared as described above in the case of the injectable solutions, it being possible to dispense with working under sterile conditions.

Solutions for use on the skin are applied dropwise, brushed on, rubbed in, splashed on sprayed on, or applied by immersion (dipping, bathing or washing). These solutions are prepared as described above in the case of the injectable solutions.

It may be advantageous to add thickeners during the preparation. Thickeners are: inorganic thickeners such as bentonites, colloidal silica, aluminium monostearate, organic thickeners such as cellulose derivatives, polyvinyl alcohols and their copolymers, acrylates and metacrylates.

Gels are applied to, or brushed onto, the skin, or introduced into body cavities. Gels are prepared by treating solutions which have been prepared as described in the case of the injectable solutions with such an mount of thickener that a clear substance of cream-like consistency is formed. Thickeners employed are the thickeners indicated further above.

Pour-on and spot-on formulations are poured onto, or splashed onto, limited areas of the skin, the active compound either penetrating the skin and acting systemically or being distributed over the body surface.

Pour-on and spot-on formulations are prepared by dissolving suspending or emulsifying the active compound in suitable solvents or solvent mixtures which are tolerated by the skin. If appropriate, other adjuvants such as colourants, absorption accelerators, antioxidants, light stabilizers and tackifiers are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, aromatic and/or aliphatic hydrocarbons, vegetable or synthetic oils, DMF, dimethylacetamide, N-methyl-pyrrolidone, 2-dimethyl-4-oxy-methylene-1,3-dioxolane.

Colourants are all colourants which are approved for use on animals and which can be dissolved or suspended.

Examples of absorption accelerators are DMSO, spreading oils such as isopropyl myristate, dipropylene glycol pelargonate, silicone oils, fatty acid esters, triglycerides, fatty alcohols.

Antioxidants are sulphites or metabisulphites such as potassium metabisulphate, ascorbic acid, butylhydroxytoluene, butylhydroxyanisole, tocopherol.

Examples of light stabilizers are substances from the class of the benzophenones or novantisolic acid.

Examples of tackifiers are cellulose derivatives, starch derivatives, polyacrylates, natural polymers such as alginates, gelatine.

Emulsions can be administered orally, dermally or in the form of injections.

Emulsions are either of the water-in-oil type or of the oil-in-water type.

They are prepared by dissolving the active compound either in the hydrophobic or in the hydrophilic phase and homogenizing this phase with the solvent of the other phase, with the aid of suitable emulsifiers and, if appropriate, other adjuvants such as colourants, absorption accelerators, preservatives, antioxidants, light stabilizers or viscosity-increasing substances.

The following may be mentioned as the hydrophobic phase (oils): paraffin oils, silicone oils, natural vegetable oils such as sesameseed oil, almond oil, castor oil, synthetic triglycerides such as caprylic/capric acid biglyceride, triglyceride mixture with vegetable fatty acid of chain length $C_{8-12}$ or with other specifically selected natural fatty acids, partial glyceride mixtures of saturated or unsaturated fatty acids which may also contain hydroxyl groups, and mono- and diglycerides of the $C_8$–$C_{10}$-fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}$–$C_{18}$, isopropyl myristate, isopropyl palmitate, cyprylic/capric esters of saturated fatty alcohols of chain length $C_{12}$–$C_{18}$, isopropyl stearate, oleyl oleate, decyl oleate, ethyl oleate, ethyl lactate, waxy fatty acid esters such as artificial duck preen fat, dibutyl phthalate, diisopropyl adipate, ester mixtures related to the latter, etc..

Fatty alcohols such as isotridecyl alcohol, 2-octyl dodecanol, cetylstearyl alcohol, oleylalcohol.

Fatty acids such as, for example, oleic acid and its mixtures.

The following may be mentioned as hydrophilic phase: water, alcohol such as, for example, propylene glycol, glycerol, sorbitol and their mixtures.

The following may be mentioned as emulsifiers: non-ionic surfactants, for example polyoxyethylated castor oil, polyoxyethylated sorbitan monooleate, sorbitan monostearate, glycerol monostearate, polyoxyethyl stearate, alkylphenol polyglycol ethers;

ampholytic surfactants such as disodium N-lauryl-β-iminodipropionate or lecithin;

anionic surfactants such as sodium lauryl sulphate, fatty alcohol ether sulphates, the monoethanol amine salt of mono/dialkylpolyglycol ether orthophosphoric esters;

cationic surfactants such as cetyltrimethylammonium ammonium chloride.

The following may be mentioned as other adjuvants: viscosity-increasing substances and substances which stabilize the emulsion, such as carboxymethylcellulose, methylcellulose and other cellulose and starch derivatives, polyacrylates, alginates, gelatine, gum arabic, polyvinylpyrrolidone, polyvinyl alcohol, copolymers of methyl vinyl ether and maleic anhydride, polyethylene glycols, waxes, colloidal silica, or mixtures of the substances mentioned.

Suspensions can be administered orally, dermally or in the form of an injection. They are prepared by suspending the active substance in an excipient liquid, if appropriate with the addition of further adjuvants such as wetting agents, colourants, absorption accelerators, preservatives, antioxidants and light stabilizers.

Excipient liquids which may be mentioned are all homogeneous solvents and solvent mixtures.

Wetting agents (dispersants) which may be mentioned are the surfactants indicated further above.

Further adjuvants which may be mentioned are those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of adjuvants, and the mixture is formulated as desired.

Excipients which may be mentioned are all physiologically acceptable solid inert substances. Suitable as such are inorganic and organic substances. Examples of inorganic substances are sodium chloride, carbonates such as calcium carbonate, hydrogen carbonates, aluminium oxides, silicas, clays, precipitated or colloidal silicon dioxide, and phosphates.

Examples of organic substances are sugars, cellulose, foods and animal feeds such as dried milk, animal meals, cereal meals and coarse cereal meals and starches.

Adjuvants are preservatives, antioxidants and colourants which have already been indicated further above.

Other suitable adjuvants are the lubricants and glidants such as, for example, magnesium stearate, stearic acid, talc, bentonites, disintegrants such as starch or cross-linked polyvinylpyrrolidone, binders such as, for example, starch, gelatine or linear polyvinylpyrrolidone, and also dry binders such as microcrystalline cellulose.

In the preparations, the active compounds can also be present in the form of a mixture with synergists or with other active compounds which act against pathogenic endoparasites. Examples of such active compounds are L-2,3,5,6-tetrahydro-6-phenylimidazolethiazole, benzimidazole carbamates, praziquantel, pyrantel, febantel.

Ready-to-use preparations contain the active compound in concentrations of 10 ppm to 20 percent by weight, preferably 0.1 to 10 percent by weight.

Preparations which are diluted prior to administration contain the active compound in concentrations of 0.5 to 90 percent by weight, preferably 5 to 50 percent by weight.

In general, it has proved advantageous to administer amounts of approximately 1 to 100 mg of active compound per kg of body weight per day, to achieve effective results.

In the examples which follow, the active compound employed is imidachloprid=1-[(6-choro-3-pyridinyl) methyl]-N-nitro-imidazolidineimine.

EXAMPLE 1

SC (suspension concentrate) formulation:
  368 g imidacloprid 35 g block copolymer of emulsifier, ethylene oxide and propylene oxide 12 g ditolyl ether sulphonate/formaldehyde condensate (emulsifier)

3.5 g water-soluble polyvinyl alcohol 58.0 g $NH_4Cl$;

116.0 g urea 1.2 g (37% strength aqueous hydrochloric acid)

4.6 g xanthan gum 560.5 g distilled water

EXAMPLE 2

WP (dispersible powder) formulation:

25.0 g of imidacloprid 1.0 g of sodium diisobutylnaphthalenesulphonate 10.0 g of calcium n-dodecylbenzenesulphonic acid 12.0 g of highly-disperse silica-containing alkylaryl polyglycol ether 3.0 g of ditolyl ether sulphonate/formaldehyde condensate (emulsifier)

2.0 g of ®Baysilon-E, a silicone-containing antifoam made by Bayer AG 2.0 g of finely-dispersed silicon dioxide and 45.0 g of kaolin

EXAMPLE 3

SL (water-soluble concentrate) formulation 18.3 g of imidacloprid 2.5 g of neutral emulsifier based on alkylaryl polyglycol ether 3.5 g of sodium diisooctyl sulphosuccinate 38.4 g of dimethyl sulphoxide and 37.5 g of 2-propanol

EXAMPLE 4

SL (water-soluble concentrate) formulation 185 g of imidaclopdd 5.0 g of sodium diisooctyl sulphosuccinate and 76.5 g of dimethyl sulphoxide are added to a 100 g of shampoo formulation composed of 44.4% by weight of Marlon AT 50, a triethanolamine salt of alkylbenzenesulphonic acids, manufactured by Hüls AG 11.1% by weight of Marlon A 350, sodium salt of alkylbenzenesulphonic acids, manufactured by Hüls AG 3.0% by weight of a condensation product of oleic acids and diethanolamine, manufactured by Hüls AG, and 41.5% by weight of polyethylene glycol.

EXAMPLE 5

Spray formulation composed of 2.0 g of imidacloprid 10.0 g of dimethyl sulphoxide 35.0 g of 2-propanol and 53.0 g of acetone cl EXAMPLE A In-vivo nematode test

*Haemonchus contortus*/sheep

Sheep which had been infected experimentally with *Haemonchus contortus* were treated after the prepatent period of the parasite had elapsed. The active compounds were applied orally in the form of pure active compound in gelatine capsules.

The degree of effectiveness is determined by quantitatively evaluating the worm eggs excreted together with the faeces before and after the treatment.

If egg excretion has stopped completely after the treatment, this means that the worms had been aborted or are damaged to such an extent that they no longer produce eggs (dosis effectiva).

Test active compounds and effective dosages (dosis effectiva) can be seen from the table which follows.

| Active compound | Dosis effectiva in mg/kg |
|---|---|
| Imidacloprid | 10 |

EXAMPLE B

Example *Hymenolepis nana*/mouse

Oral experimental infection with infectious eggs from proglottids. Treatment is effected after the prepatent period has elapsed (4 times, on 4 subsequent days, oral). After 7 days, the number of scolices in the gut is determined. The effectiveness is calculated using the formula $$\% \text{ Effectiveness} = \frac{\text{Number of scolices in the control group} - \text{number of scolices of the treated group}}{\text{Number of scolices in the control group}}$$

Active compound: imidacloprid; effectiveness: 100 % when 25 mg/kg are administered only.

We claim:

1. A method of combating endoparasites in a warm-blooded animal infected with said endoparasites, said method comprising administering to said warm-blooded animal an endoparasiticidally effective amount of an agonist or antagonist of the nicotinergic acetylcholine receptor of an insect of the formula:

$$R-N\begin{matrix}(A)\\ \diagdown \\ C \\ \| \\ X-E\end{matrix}\begin{matrix}\diagup (Z)\end{matrix} \qquad (I)$$

which

R represents hydrogen, and optionally substituted radicals selected from the group consisting of acyl, alkyl, aryl, aralkyl, heteroaryl or heteroarylalkyl, A represents a monofunctional group selected from the group consisting of hydrogen, acyl, alkyl and aryl or represents a bifunctional group linked to the radical Z, wherein the bifunctional group is optionally interrupted by heteroatoms selected from the group consisting of N, O and S, E represents an electron-attracting radical, X represents the radicals —CH=, =N—, or the radical $$\overset{|}{-}C=$$

linked to the radical Z,

Z represents a monofunctional group selected from the group consisting of alkyl, —O—R, —S—R,

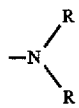

or represents a bifunctional group linked to the radical A or the radical X.

2. A method according to claim 1, wherein under the definition of R, acyl radicals represents formyl, alkylcarbonyl, arylcarbonyl, alkylsulphonyl, arylsulphonyl, (alkyl-)-(aryl)-phosphoryl, each optionally substituted,

- alkyl radicals represents straight or branched $C_{1-10}$-alkyl, each optionally substituted,
- aryl radicals represents phenyl and naphthyl, each optionally substituted,
- aralkyl radicals represents phenylmethyl and phenethyl, each optionally substituted,
- heteroaryl radicals represents heteroaryl having up to 10 ring atoms and heteroatoms of at least one of N, O and S, optionally substituted,
- heteroarylalkyl radicals represents heteroarylmethyl and heteroarylethyl having up to 6 ring atoms and at least one of N, O and S, optionally substituted.

3. A method according to claim 1, wherein alkyl radicals represent $C_{1-4}$-alkyl, each optionally substituted.

4. A method according to claim 2, wherein the heteroatom of the heteroaryl is N.

5. A method according to claim 2, wherein heteroaryl represents thienyl, furyl, thiazolyl, imidazolyl, pyridyl, or benzthiazolyl, each optionally substituted.

6. A method according to claim 2, wherein the heteroatom of the heteroarylalkyl is N.

7. A method according to claim 1, wherein under the definition of A,

- acyl radicals represents formyl, alkylcarbonyl, arylcarbonyl, alkylsulphonyl, arylsulphonyl, (alkyl-)-(aryl)-phosphoryl, each optionally substituted,
- alkyl radicals represents straight or branched $C_{1-10}$-alkyl, each optionally substituted,
- aryl radicals represents phenyl and naphthyl
- or a bifunctional group represented by optionally substituted $C_1-C_4$ alkylene optionally interrupted by at least one heteroatom wherein the heteroatoms represent N, O and S.

8. A method according to claim 7, wherein alkylene is $C_1-C_2$ alkylene.

9. A method according to claim 2, wherein A and Z together with the atoms to which they are bonded form a saturated or unsaturated 5 to 7 membered heterocyclic ring, optionally being interrupted by additional heteroatoms other than the N in the formula chain wherein the additional heteroatoms represent N, O or S.

10. A method according to claim 2, wherein A and Z together with the atoms to which they are bonded form a saturated or unsaturated 5 to 7 membered heterocyclic ring being interrupted by a heterogroup.

11. A method according to claim 10, wherein said heterogroup is N-alkyl wherein alkyl represents straight or branched $C_1-C_4$-alkyl.

12. A method according to claim 11, wherein said agonist or antagonist is a compound represented by the formulae:

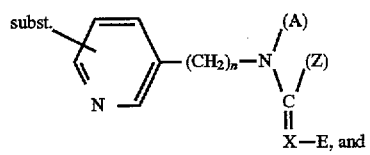

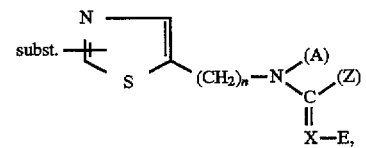

in which n represents 1 or 2, subst. represents one of the abovementioned substituents.

13. A method according to claim 12, wherein subst. represents halogen.

14. A method according to claim 1, wherein the optional substituents are selected from the group consisting of alkyl, alkoxy, alkylthio, haloalkyl, hydroxyl, halogen, cyano, nitro, amino, mono and dialkylamino, carboxyl, carbalkoxy, sulpho, alkylsulphonyl, arylsulphonyl, heteroarylamino, and heteroarylalkylamino.

15. A method according to claim 1, wherein the optional substituents are selected from the group consisting of $C_1-C_4$-alkyl, $C_1-C_4$-alkoxy, $C_1-C_4$-alkylthio, $C_1-C_4$-haloalkyl having 1 to 5 haloatoms, hydroxyl, halogen of fluorine, chlorine, bromine or iodine, cyano, nitro, amino, $C_1-C_4$-monoalkylamino, $C_1-C_4$-dialkylamino, carboxyl, $C_1-C_4$-carbalkoxy, sulpho, $C_1-C_4$-alkylsulphonyl, arylsulphonyl having 6 or 10 aryl carbon atoms, heteroarylamino and heteroarylkylamino.

16. A method according to claim 15, wherein the optional substituents are selected from the group consisting of alkyl having 1 or 2 carbon atoms, alkoxy having 1 or 2 carbon atoms, alkylthio having 1 or 2 carbon atoms, halogenoalkyl having 1 or 2 carbon atoms and 1 to 3 halogen atoms, the halogen atoms being identical or different and being represented by fluorine, chlorine or bromine; monoalkyl- and dialkylamino having 1 or 2 carbon atoms per alkyl group, carbalkoxy having 1 or 2 carbon atoms; and alkylsulphonyl having 1 or 2 carbon atoms.

17. A method according to claim 1, wherein the optional substituents are selected from the group consisting of methyl, ethyl, n- and i-propyl and n-, i- and t-butyl; methoxy, ethoxy, n- and i-propyloxy and n-, i- and t-butyloxy; methylthio, ethylthio, n- and i-propylthio, and n-, i- and t-butylthio, halogenoalkyl having 1 to 2 carbon atoms, the halogen atom being represented by fluorine; hydroxyl, fluorine, chlorine and bromine; cyano, nitro, amino, methylamino, methyl-ethyl-amino, n- and i-propylamino and methyl-n-butylamino, carboxyl, carbomethoxy and carboethoxy; methylsulphonyl and ethylsulphonyl, phenylsulphonyl, and chloropyridylamino and chloropyridylmethylamino.

18. A method according to claim 17, wherein the haloalkyl is trifluoromethyl.

19. A method according to clam 1, wherein said agonist or antagonist is at least one of the compounds selected from the group consisting of:

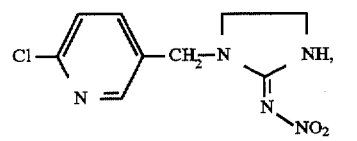
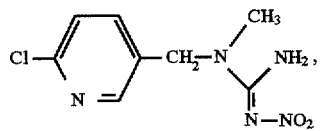
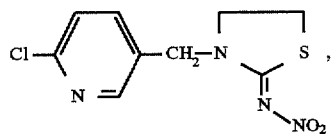
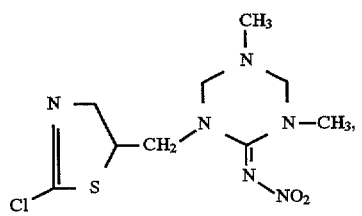
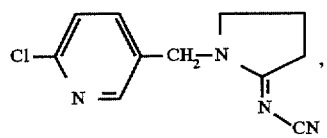
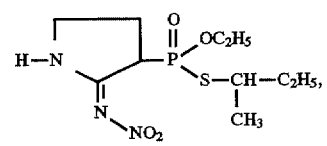
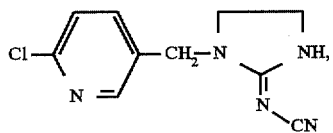
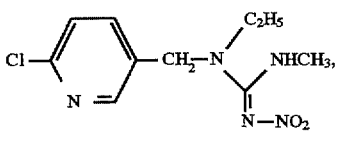
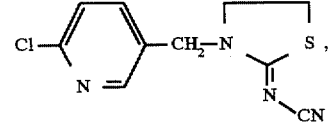
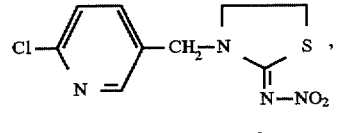
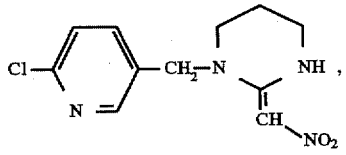
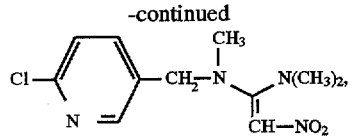
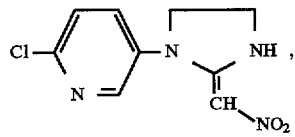
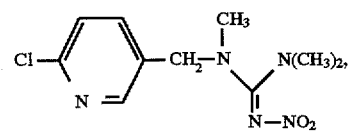
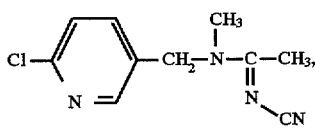
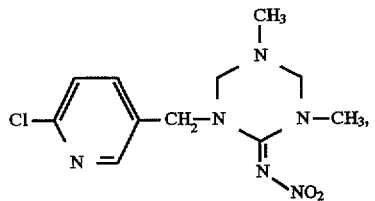
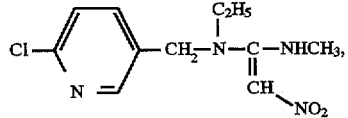
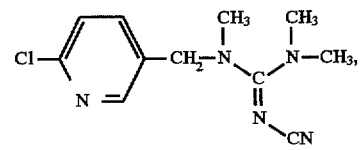
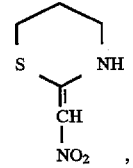
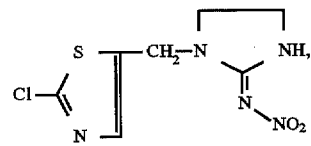
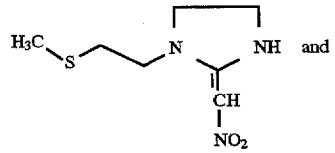

-continued
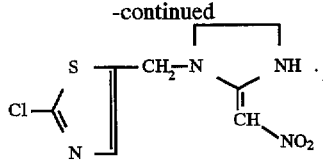
20. A method according to claim 1, wherein said agonist or antagonist is imidachloprid.
* * * * *